US006692464B2

(12) United States Patent
Graf

(10) Patent No.: US 6,692,464 B2
(45) Date of Patent: Feb. 17, 2004

(54) T-FITTING FOR SPLITTABLE SHEATH

(75) Inventor: Matthew M. Graf, Bloomington, IN (US)

(73) Assignee: Cook, Incorporated, Bloomington, IN (US)

( * ) Notice: Subject to any disclaimer, the term of this patent is extended or adjusted under 35 U.S.C. 154(b) by 0 days.

(21) Appl. No.: 10/085,873

(22) Filed: Feb. 28, 2002

(65) Prior Publication Data

US 2003/0163139 A1 Aug. 28, 2003

(51) Int. Cl.[7] .......................... A61M 5/178; A61M 5/32
(52) U.S. Cl. ................ 604/160; 604/164.05; 604/163; 604/164.08
(58) Field of Search ................ 604/160, 161, 604/164.01, 164.05, 170.02, 163, 164.08, 171

(56) References Cited

U.S. PATENT DOCUMENTS

| | | | |
|---|---|---|---|
| 4,449,973 A | 5/1984 | Luther | |
| RE31,855 E | 3/1985 | Osborne | |
| 4,596,559 A | * 6/1986 | Fleischhacker | 604/164.05 |
| 4,772,266 A | 9/1988 | Groshong | |
| 5,098,392 A | 3/1992 | Fleischhacker et al. | |
| 5,141,497 A | 8/1992 | Erskine | |
| 5,167,634 A | 12/1992 | Corrigan, Jr. et al. | |
| 5,250,033 A | 10/1993 | Evans et al. | |
| 5,304,142 A | 4/1994 | Liebl et al. | |
| 5,312,355 A | 5/1994 | Lee | |
| 5,391,152 A | * 2/1995 | Patterson | 604/165.04 |
| 5,409,469 A | 4/1995 | Schaerf | |
| 5,441,504 A | 8/1995 | Pohndorf et al. | |
| 5,536,255 A | 7/1996 | Moss | |
| 5,672,158 A | 9/1997 | Okada et al. | |
| 5,685,856 A | 11/1997 | Lehrer | |
| 5,713,867 A | 2/1998 | Morris | |
| 5,735,819 A | 4/1998 | Elliott | |
| 5,741,233 A | 4/1998 | Riddle et al. | |
| 5,772,678 A | 6/1998 | Thomason et al. | |
| 5,782,807 A | 7/1998 | Falvai et al. | |
| 5,885,217 A | 3/1999 | Gisselberg et al. | |
| 5,971,958 A | * 10/1999 | Zhang | 604/165.02 |
| 6,027,480 A | 2/2000 | Davis et al. | |
| 6,210,366 B1 | 4/2001 | Sanfilippo, II | |
| 6,228,062 B1 | 5/2001 | Howell et al. | |
| D450,839 S | * 11/2001 | Junker | D24/130 |

* cited by examiner

Primary Examiner—Michael J. Hayes
Assistant Examiner—Lina R Kontos
(74) Attorney, Agent, or Firm—Brinks Hofer Gilson & Lione

(57) ABSTRACT

A splittable sheath assembly including a sheath, a T-shaped fitting and an attachment mechanism. The sheath is adapted for use in the trans-cutaneous insertion of medical instrumentation through a lumen defined by the sheath and has a distal end and a proximal end, the proximal end including an initial bifurcated portion defining two tabs. The T-shaped fitting has a central opening aligned with the lumen of the sheath, a handle on either side of the central opening, and a zone of weakness unitarily joining the two handles so that the T-shaped fitting is adapted to be split into two separate portions, each portion having only one of the handles. The attachment mechanism attaches each of the tabs of the proximal end of the sheath to one of the handles. Each attachment mechanism includes a projection portion engaging one of the tabs and a locking element received on the projection to inhibit removal of the tab from the projection. The attachment mechanism and tabs are embedded in the handles of the T-shaped fitting by insert molding the T-shaped fitting including the splittable handles around the attachment mechanisms. The molded T-shaped fitting includes locking feature for receiving a dilator fitting that is oriented to reduce any forces that might otherwise cause premature splitting of the fitting.

29 Claims, 9 Drawing Sheets

T-FITTING FOR SPLITTABLE SHEATH

BACKGROUND OF THE INVENTION

The present invention relates generally to medical devices and more particularly to introducer sheaths that are used for the transcutaneous introduction of catheters and other apparatus into a patient. The present invention relates more particularly to fittings on the proximal end of such introducer sheaths that permit the introducer sheath to be easily removed when no longer needed for the procedure.

Introducer sheaths are commonly used in various medical procedures where a catheter is transcutaneously introduced into an interior body lumen or cavity, such as a blood vessel or a hollow body organ. Typically, the introducer sheath comprises a thin-walled sheath tube that is introduced through a previously formed needle penetration. The introducer sheath can be introduced together with an internal stylet or obturator, where the stylet or obturator has a tapered distal end that extends from the sheath and dilates the previously formed hole as the sheath is advanced. After the combination of the sheath and stylet/obturator has been introduced, the stylet/obturator is removed, leaving a working channel defined by the axial lumen of the sheath. Catheters and other working devices can then be introduced through the working channel to perform various medical procedures.

Various improvements in the design of such introducer sheaths have been proposed. Of particular interest to the present invention, introducer sheaths have been designed where the sheath is weakened along opposed axial lines to facilitate splitting when the proximal end of the sheath is pulled apart. Splittable introducer sheaths can also be formed of materials, like poly-tetrafluoroethylene (TFE), having inherent molecular structure facilitating splitting of the sheath even in the absence of any structural weakening, as disclosed in U.S. Pat. No. Re31,885. Both forms of splittable sheaths are useful when it is desirable to remove the sheath from around a catheter or other device that is to remain in place in the transcutaneous penetration. In general, the proximal end of the sheath has a short longitudinal "starter" slit that initiates the splitting or peeling action by which the sheath may split or pulled apart as it is withdrawn, thus facilitating its removal. Without the ability to peel away the sheath, it would be impossible to remove the sheath over any enlarged proximal hub or housing on the catheter or other device that is intended to remain in place. The short longitudinal "starter" slits form a pair of flaps or tabs to which small knobs can be attached to facilitate the gripping of the tabs when the removal of the sheath is desired. In some prior art devices, such as are shown in U.S. Pat. Nos. 5,250,033; 5,098,392 and 4,596,559, the tabs have taken the form of a splittable T-shaped fitting molded onto the proximal end of the sheath. The combination of such prior art splittable T-shaped fittings molded together with sheaths formed of TFE has proven to be impossible due to the slickness of the TFE.

It has been suggested in U.S. Pat. No. 4,596,559 to form a splittable T-shaped fitting that mechanically engages the flaps or tabs at the proximal end of the sheath. The fitting includes pins that are intended to extend through holes in the flaps or tabs of the sheath. Hinged portions of the T-shaped fitting are intended to hinge over the tabs or flaps and engage the pins so that the tabs are captured between the hinged portions. However, the actual assembly of the structure disclosed in U.S. Pat. No. 4,596,559 is not possible without prematurely splitting the handle along the zone of reduced thickness, thus significantly reducing the structural integrity of the combined structure to the point that it is no longer serviceable in the intended manner.

The present invention is directed to a novel structure for a splittable T-shaped fitting that includes a mechanical capture of the sheath tabs while retaining all the structural integrity required to perform the desired functions including locking engagement with a dilator fitting. The present invention is particularly suitable for use with sheaths made of TFE or other slick materials, but can be used with sheaths made of any material. The present invention also includes a low stress engagement feature to engage a dilator fitting that includes a tactile report of engagement with the dilator fitting.

SUMMARY OF THE INVENTION

A splittable sheath assembly of the present invention includes a sheath, a T-shaped fitting and an attachment mechanism. The sheath is adapted for use in the transcutaneous insertion of medical instrumentation through a lumen defined by the sheath and has a distal end and a proximal end. The proximal end includes an initial bifurcated portion defining two tabs. The T-shaped fitting has a central opening aligned with the lumen of the sheath and a handle on either side of the central opening. A zone of weakness separates the two handles so that the T-shaped fitting is adapted to be split into two separate portions, each portion having only one of the handles. The attachment mechanism attaches each of the tabs of the proximal end of the sheath to one of the handles.

Each attachment mechanism includes a projection at least engaging a portion of one of the tabs. A locking element is received over the projection to inhibit movement of the tab relative to the projection. Each attachment mechanism is embedded in the T-shaped fitting so that each portion of the T-shaped fitting is coupled to only one of the sheath tabs. The attachment mechanisms can be encapsulated in the handles of the T-shaped fitting by insert molding the splittable handles around the attachment mechanisms using casting, injection molding or compression molding techniques. The polymers suitable for use as the T-shaped fitting include both thermoset and thermoplastic resins. The attachment mechanism is preferably formed as a unitary element including a hinge portion between a projection supporting portion and the locking element so that the locking element can be folded over on top of the projection-supporting portion so as to capture one of the tabs of the proximal end of the sheath. Materials suitable for use as the attachment mechanism include a wide variety of injection-moldable thermoplastic resins. Preferably the resins employed for the T-shaped fitting and the attachment mechanisms are selected to be compatible with each other during the embedding process.

The projecting portion can take the form of a peg suitable to be received in a preformed hole in the tab, or a pin suitable to puncture a hole in the tab. The projecting portion can also take the form of a series of teeth received in inter-dental spaces, ridges received in furrows, or other patterns of projections and corresponding recesses, the recesses being generally found on the coupling portion of the attachment mechanism. The projection can be suitably configured to engage the coupling portion. Alternatively, the coupling portion can be at least temporarily engaged by a separate locking flap so that the sheath tab can be retained in position during the insert molding process. Alternatively still, the coupling portion can be held in a clamping position relative to the sheath tabs by structural elements of the mold in which the insert molding process takes place.

The T-shaped fitting is preferably molded to include a snap feature adapted to receive a dilator fitting. The snap feature is defined by a pair of short ridges in the lumen of the T-shaped fitting, the pair of ridges being situated generally along the line of the zone of weakness between the two handles. This orientation for the ridges coupled with their short length minimizes the forces applied to the fitting, particularly in the direction that would cause the handles to separate, thus avoiding any premature splitting of the handles by any insertion of a dilator fitting into the lumen of the T-shaped fitting. The short ridges preferably located on opposite sides of the lumen from each other. The short ridges preferably occupy only about 30° of arc around the inside of the lumen, and are skewed from the plane defined by the zone of weakness by only about 15°. A dilator hub designed for engagement with the short ridges of the T-shaped fitting includes a peripheral engagement ring situated on a forward portion of the hub that will preferably snap fit into place without placing undue strain on the T-shaped fitting. The snap fit allows for quick insertion by the physician and a tactile signal of engagement to the physician.

While certain features and advantages of the present invention has been identified generally in the forgoing discussion, additional features and advantages will become apparent to those skilled in the art from the following description of a preferred embodiment of the invention, which references the accompanying drawings and discloses the best mode of the invention as present perceived.

DESCRIPTION OF THE PREFERRED EMBODIMENTS

Figure 1:
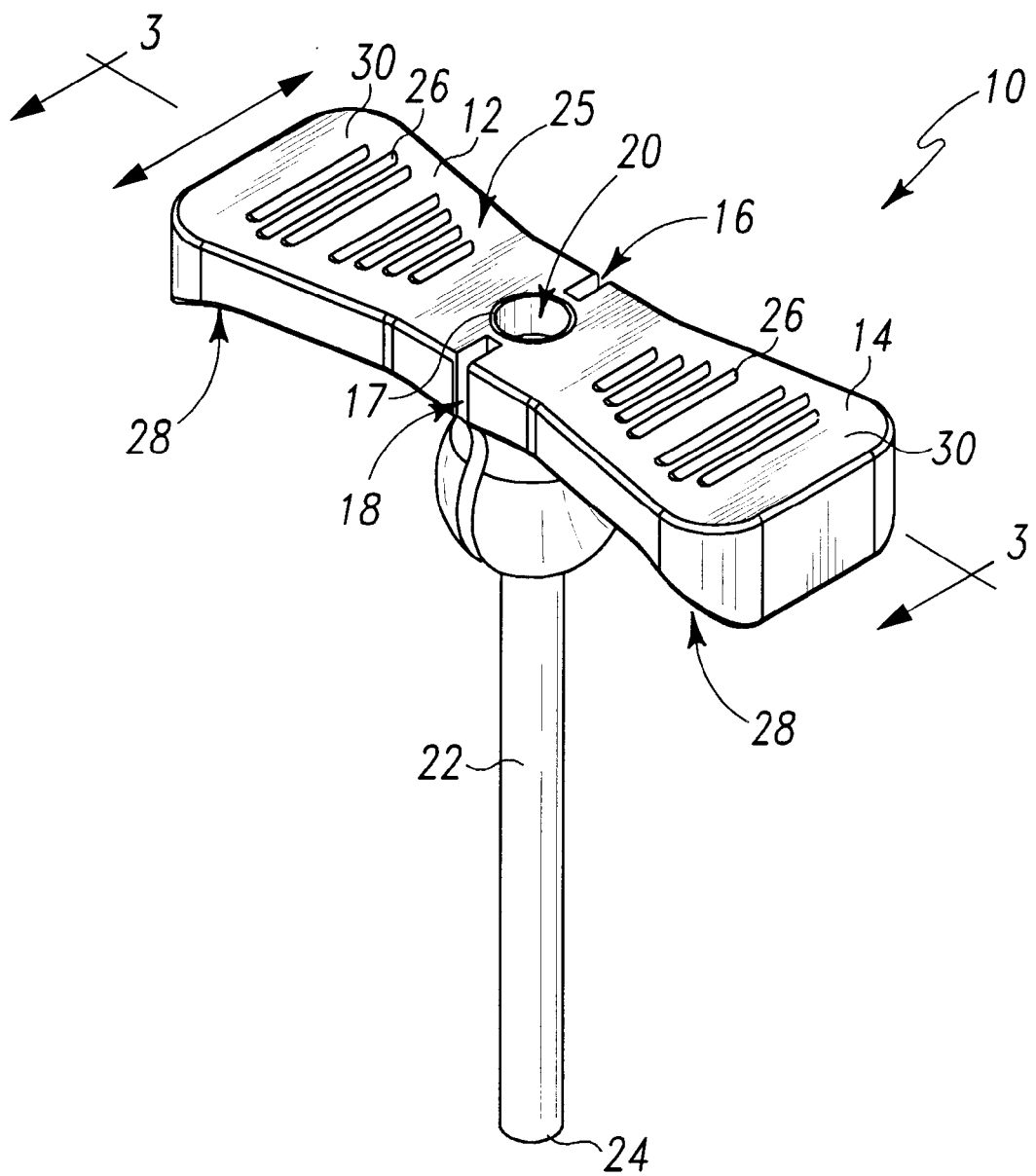
FIG. 1 is a perspective view of a T-shaped fitting of the present invention at the proximal end of a splittable sheath.

A T-shaped fitting 10 of the present invention is shown in FIG. 1 to include a left-handle portion 12, a right-handle portion 14 that are formed as a single unit. A pair of slots 16 and 18 define a zone of weakness 17 facilitating the two handles 12 and 14 being broken apart from each other. The fitting 10 includes a central channel or lumen 20 that is aligned with the interior of a sheath 22. The sheath 22 includes a distal end 24 and a proximal end, which is located inside the T-shaped fitting 10. Each of the handle portions 12 and 14 include a plurality of upstanding ridges 26 on top surface 25 of the fitting 10 that facilitate the manipulation of the T-shaped fitting and the splitting of the two handled portions 12 and 14 from each other. The T-shaped fitting 10 is formed by molding the structure in a suitable mold, preferably from a plastic that, when molded, has the same general physical characteristics as high-density polyethylene. The handle portions 12 and 14 also include downwardly sloped lower surfaces 28 to facilitate the handling the fitting 10. The handles 12 and 14 also have an outside end portion 30 which has a lateral dimension L greater than at the zone of weakness 17 at the unitary junction of the handles 12 and 14 so that the fitting 10 generally has a butterfly conformation.

Figure 2:
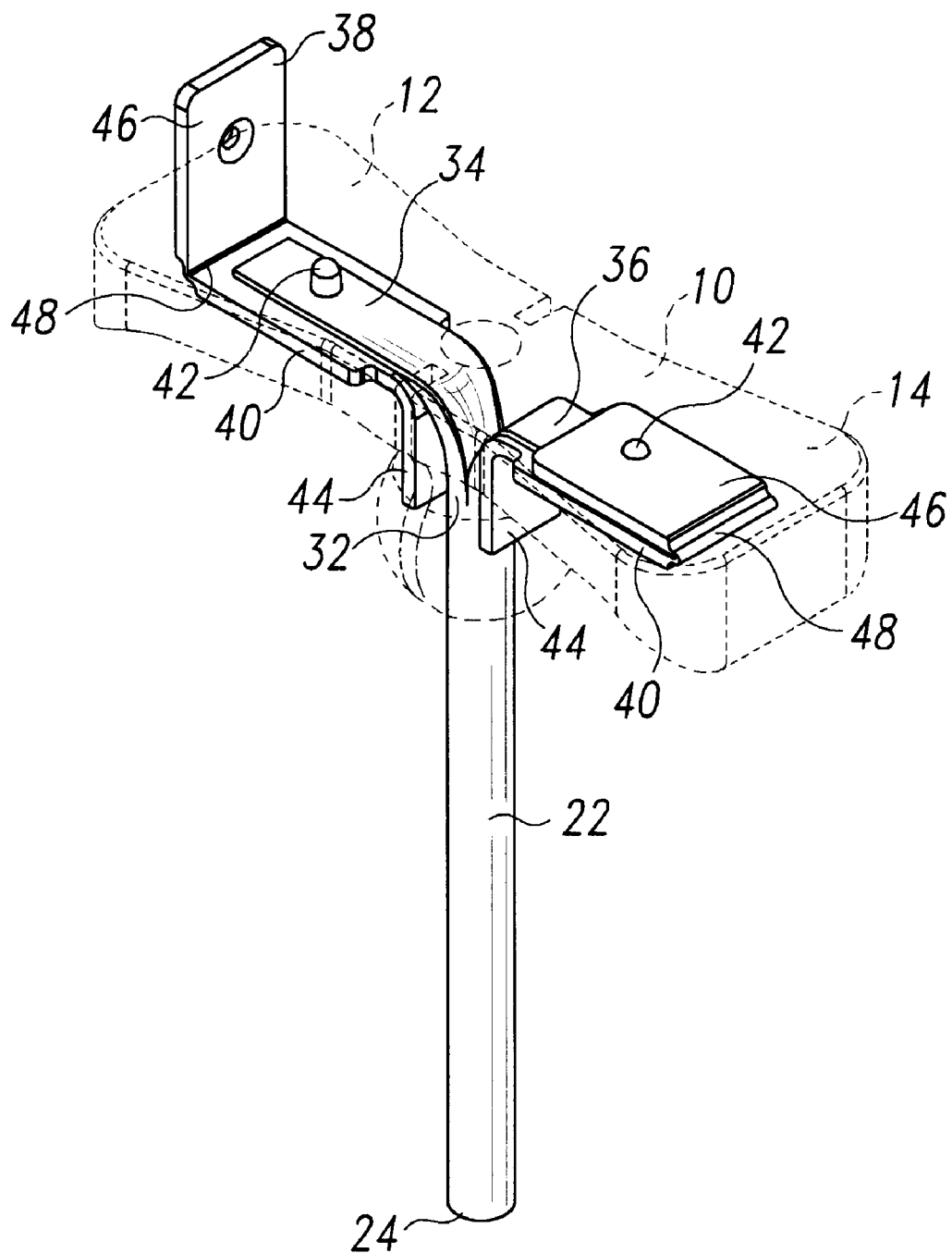
FIG. 2 is a view similar to FIG. 1 with the molded portion of the T-shaped fitting shown in phantom to reveal a pair of attachment mechanisms engaging the tab portions of the split proximal end of the sheath.

FIG. 2 shows the molded T-shaped fitting 10 of FIG. 1 in phantom to reveal additional portions of the total structure which are imbedded in the molded handle portions 12 and 14. The sheath 22 includes not only the distal end 24 but also a proximal end 32 that is bifurcated to form to tabs 34 and 36. Each of the tabs 34 and 36 is received in an attachment mechanism 38. The attachment mechanism 38 includes a first portion 40 that supports a projection 42. In FIG. 2, the projection 42 can be seen to extend through tab 34 of sheath 22. The attachment mechanism 38 also includes an angled portion 44 that extends downwardly generally parallel to the sheath 22. The attachment mechanism 38 also includes a locking portion 46 that is joined to portion 40 by a unitary hinge 48. The hinge 48 permits the locking portion 46 to be folded over the tab 34 or 36 so as to secure the tab between the locking portion 46 and the projection supporting portion 40 of the attachment mechanism 38.

Figure 3:
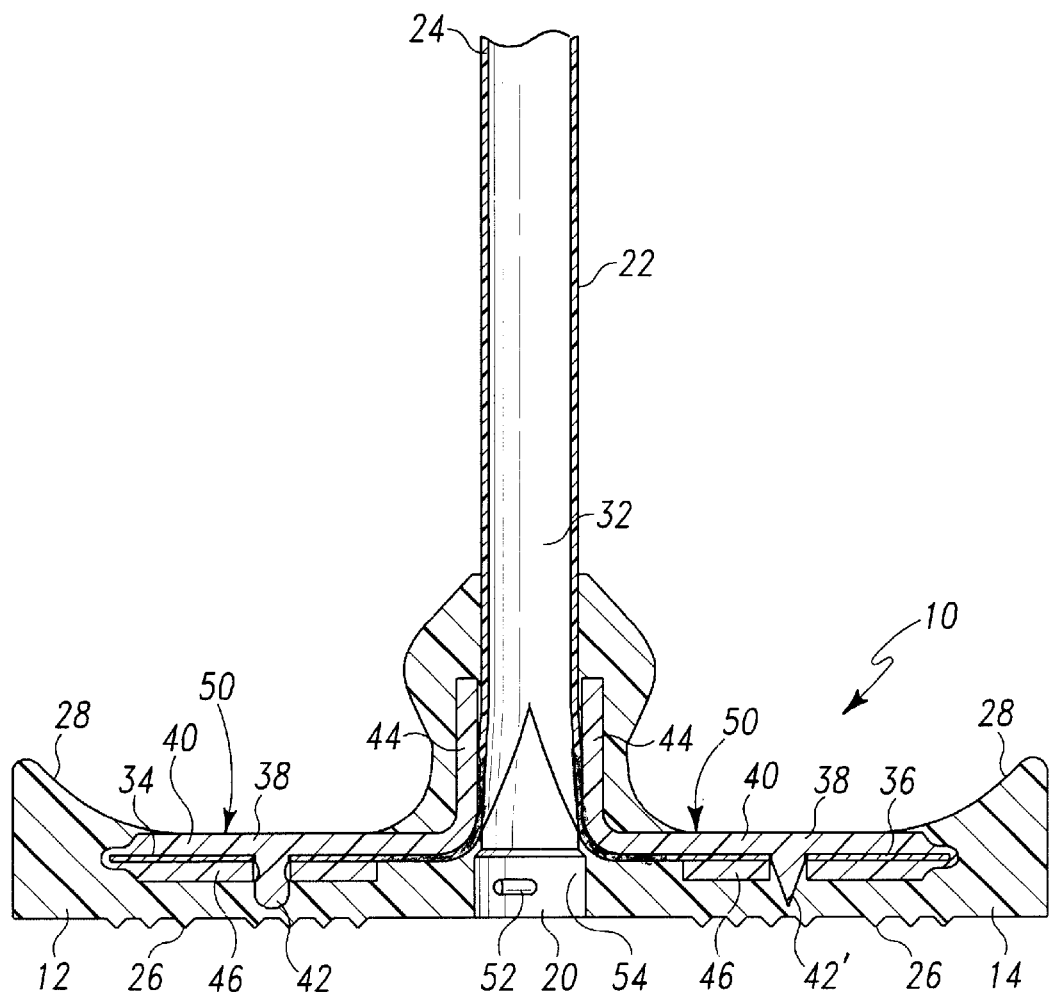
FIG. 3 is a sectional view of the T-shaped fitting shown in FIGS. 1 and 2 showing two embodiments of the projection portion of the attachment mechanisms.

It will be seen in the sectional view shown in FIG. 3 that a distal-facing surface 50 of the attachment mechanisms 38 may be exposed even though the remaining portions of the attachment mechanism 38 are completely imbedded within the material forming the handles 12 and 14. Additionally, the projection portions 42 can have different confirmations. A rounded or bulbous end confirmation for projection 42 is shown within handle 12, while a more pointed penetrating end 42' is shown embedded within handle 14. It will be appreciated that the more pointed confirmation of projection 42' permits utilization of an attachment mechanism without pre-formation of a hole in the tab of sheath 22. FIG. 3 also shows a raised area 52 on an inside surface 54 of the central opening 20 in the T-shaped fitting 10. The raised area 52 is intended to facilitate engagement with other medical instrumentation.

Figure 4A:
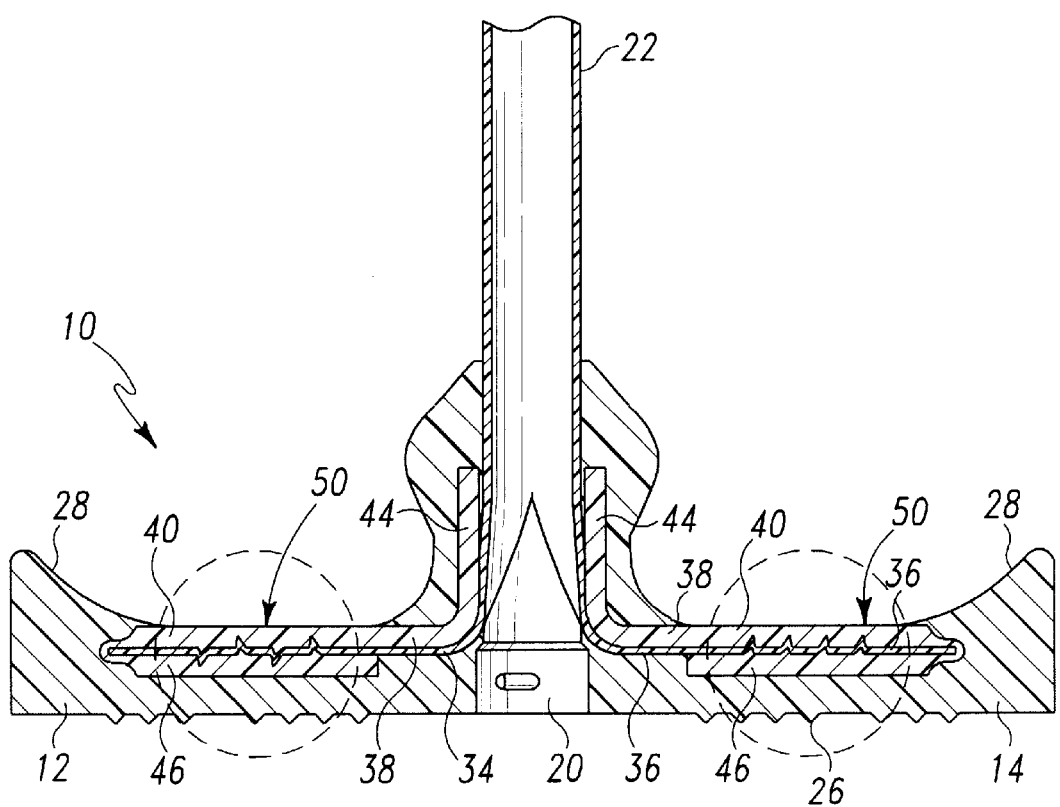
FIG. 4A is a sectional view of the T-shaped fitting similar to FIG. 3 showing two further embodiments of the projection portion of the attachment mechanisms.
Figure 4B:
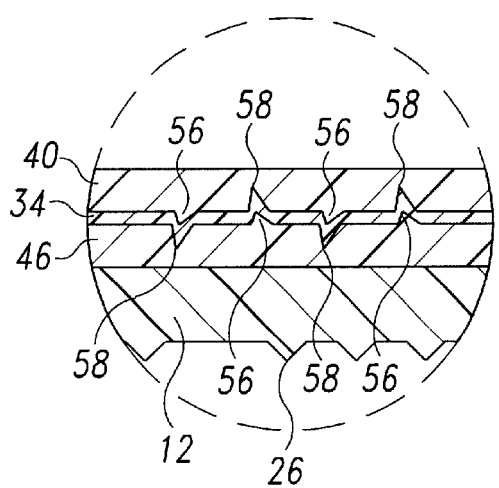
FIGS. 4B and 4C are sectional detail views taken from FIG. 4A.
Figure 4C:
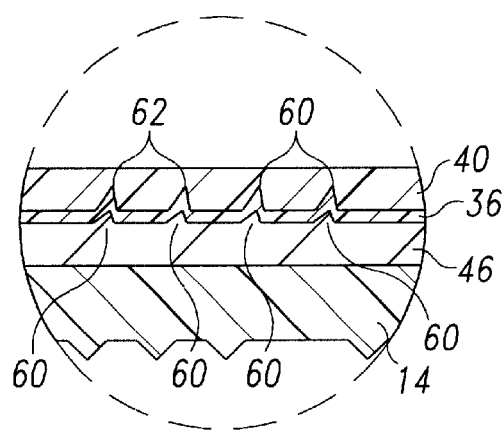

FIGS. 4A, 4B and 4C show two additional alternate embodiments for the projections on the attachment mechanism 38 that is imbedded within the T-shaped fitting 10. In the embodiment shown on the left side of FIG. 4A and in FIG. 4B, the projections 42 comprise a series of ridges 56 and furrows 58 that are alternately positioned on portion 40 and 46 of the attachment mechanism 38. On the right side of FIG. 4A and in FIG. 4C, the projections take the form of a series of teeth 60 on portion 46 that project into spaces 62 on portion 40 of attachment mechanism 38. In both the variations shown in FIGS. 4B and 4C, the tabs 34 and 36 are clamped between the portions 40 and 46 of the attachment mechanism 38. In all of the embodiments, the T-shaped fitting 10 is molded around the attachment mechanisms 38, preferably by an insert molding process, so that the attachment mechanisms 38 and T-shaped fitting 10 are intimately joined together and fixed to each other.

Figure 5:
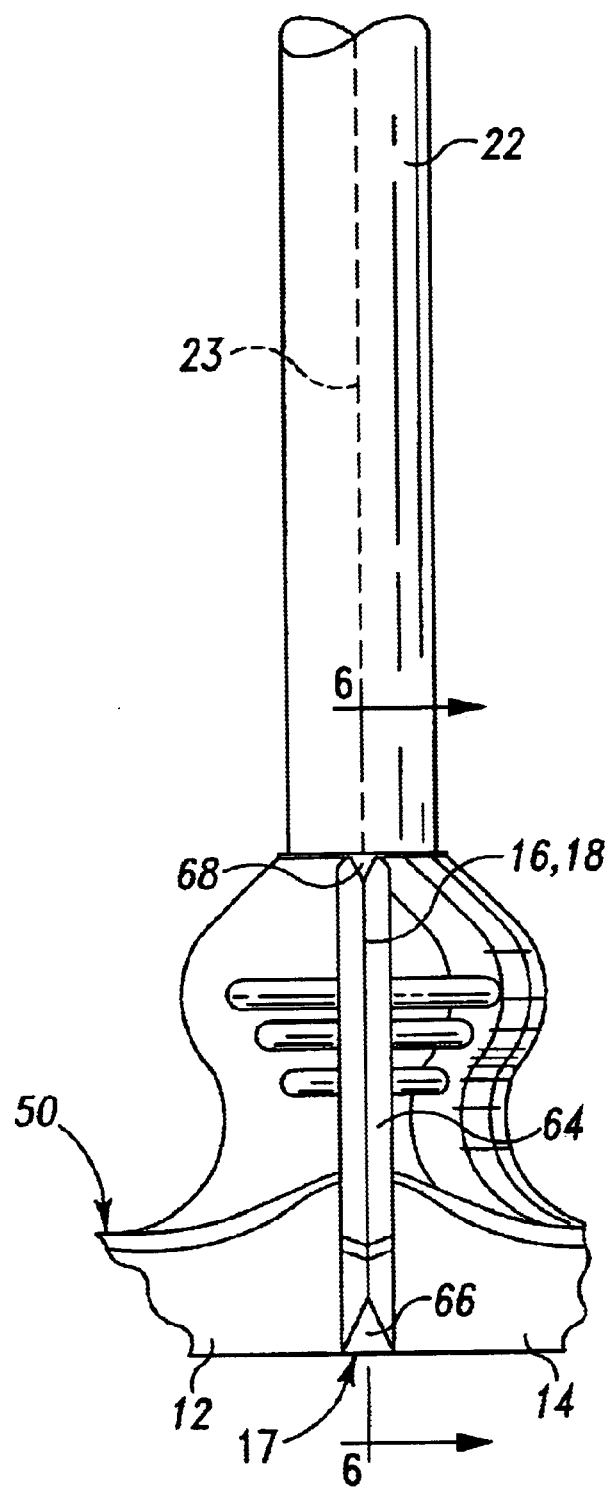
FIG. 5 is a side elevation view of the weakened zone formed in a T-shaped fitting of the present invention.
Figure 6:
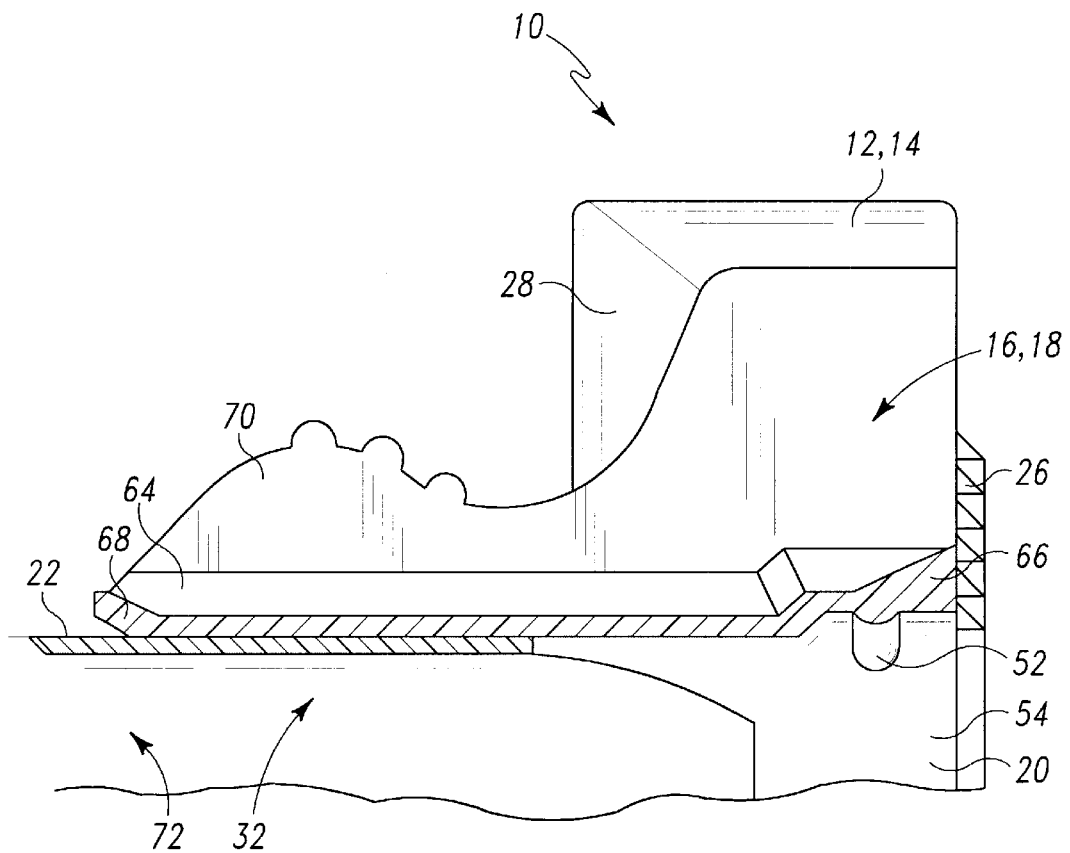
FIG. 6 is a detail sectional view taken along line 6—6 of FIG. 5.

FIG. 5 shows a particularly advantageous confirmation for the slots 16 and 18 separating handle portions 12 and 14. The slot 16 includes a V-shaped bottom portion 64 defining the zone of weakness 17 that facilitates the separation of the handles 12 and 14 from each other. The sheath 22 can include scoring 23 aligned with the zone of weakness 17. The V-shaped slot 64 has upwardly inclined end portions 66 and 68 that constitute thin joining sections between handles 12 and 14. The strength required to separate the handles 12 and 14 can be controlled by controlling the size and dimension of the ribs 66 and 68. This can be appreciated by viewing the sectional view shown in FIG. 6 which is taken from FIG. 5. One-half of the V-shaped section of the slot 64 is shown along with the joining portion including the end portion 68 and 66 in section. FIG. 6 also shows the downwardly tapering surface 28 of handle 14 and the ridges 26 on the top of handle 14. It will further be seen that the slot 16 or 18 includes a parallel wall portions 70 that define a major portion of the slots 16 and 18, which can also be seen in FIG. 1. It will be noted that the interior surface 54 of the axial opening 20 and in the T-shaped fitting 10 is aligned with the interior surface 72 of lumen 22 and that the bifurcated portions of the lumen 22 forming the tabs 34 and 36 are imbedded into the plastic forming the handles 12 and 14 of the fitting 10.

Figure 7:
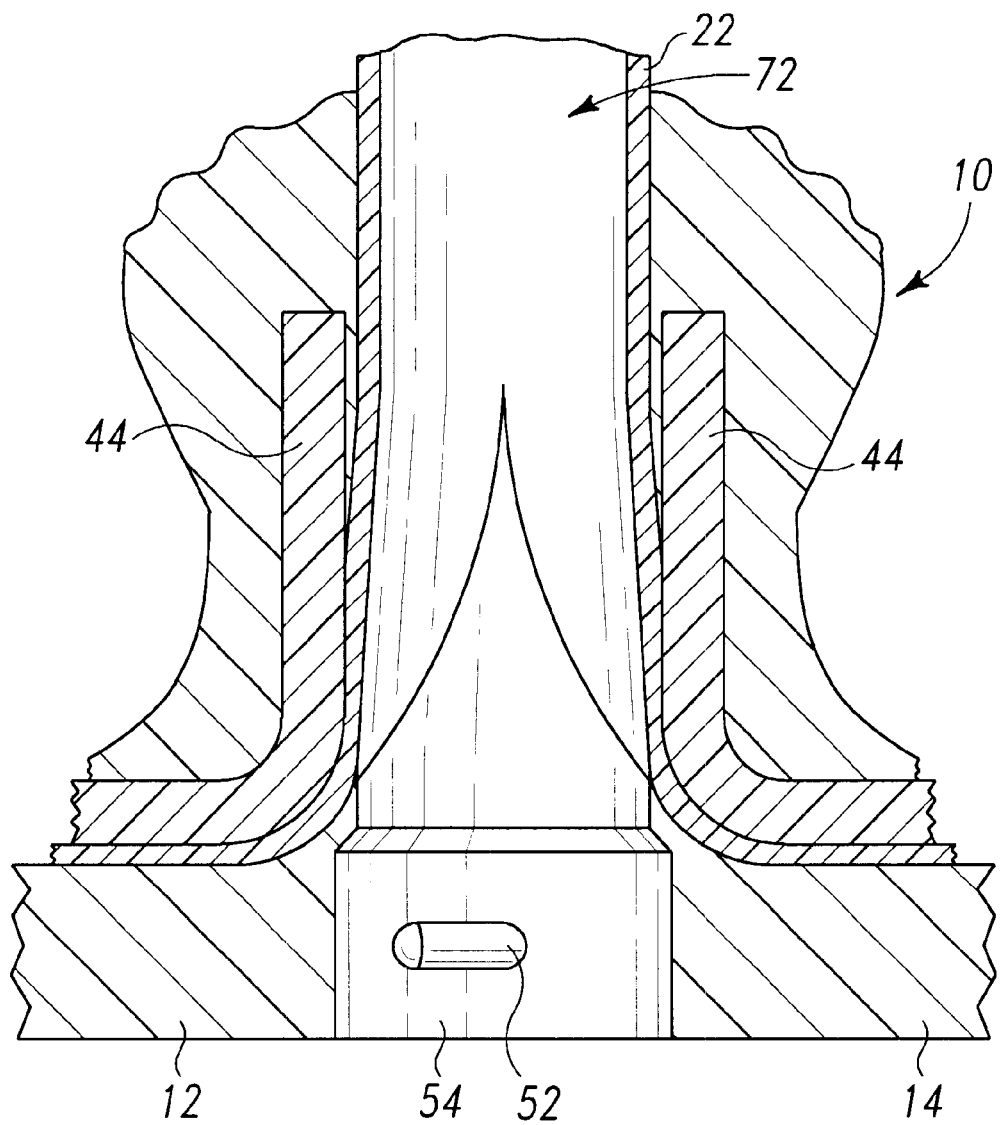
FIG. 7 is a detail sectional view of a central portion of FIG. 4A.
Figure 8:
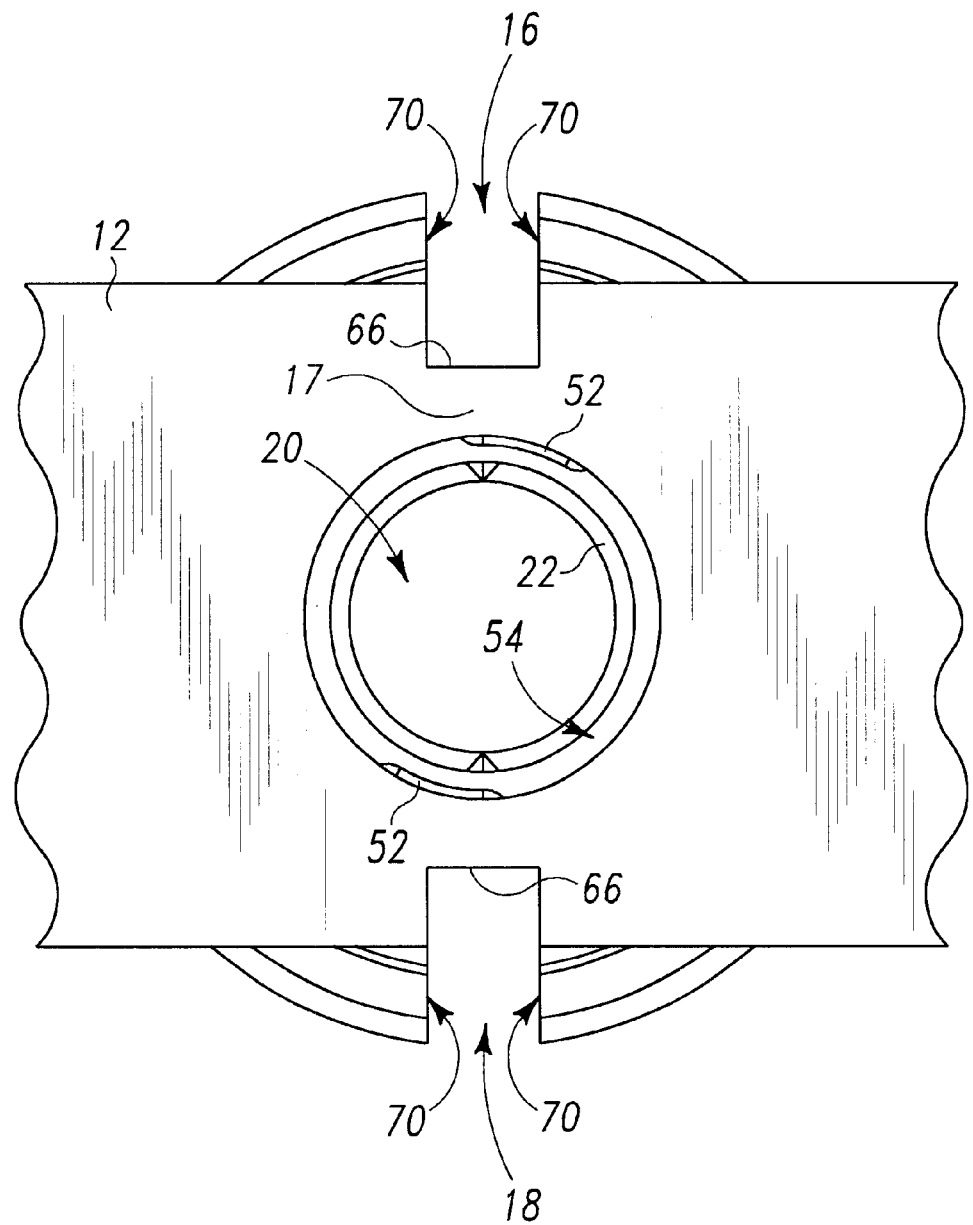
FIG. 8 is an end elevation view showing the relationship between the weakened portion of the T-shaped fitting and the dilator engagement feature.

The raised area 52 is shown to be positioned on the inside surface 54 of the axial opening 20 adjacent to the slot 16 and 18. This is also shown in FIGS. 7 and 8, where it will be seen that the raised area 52 is confined to an arc of about 30° from a line in direct alignment with slots 16 and 18. This positioning ensures that any outward force exerted on the raised area 52 will exert only minimal force tending to break the handles 12 and 14 apart. Were the raised areas 52 to be located at 90° to the plane of the groove 16 and 18, the force of insertion of another instrument into engagement with the raised areas 52 could conceivably be sufficient to break the joining portion 66 coupling the handle portions 12 and 14 together.

Figure 9:
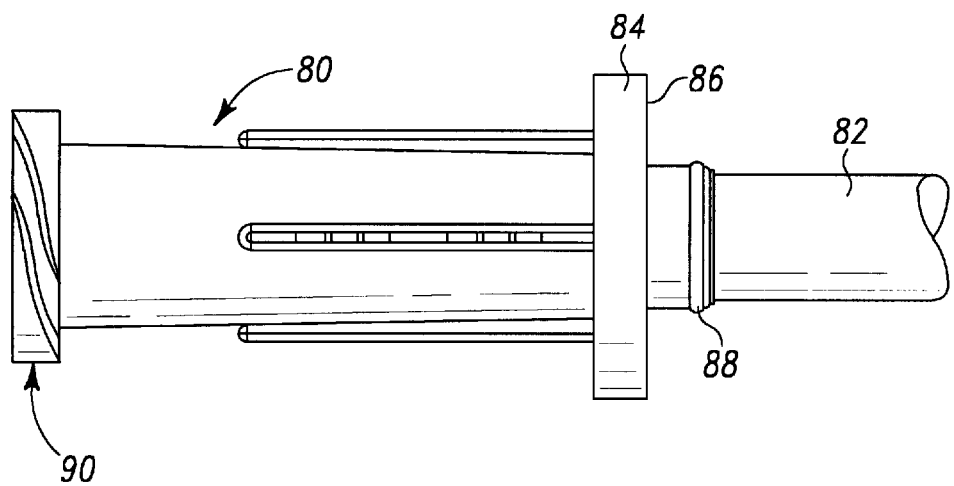
FIG. 9 is a side elevation view of a dilator hub designed for engagement with the T-shaped fitting of the present invention.
Figure 10:
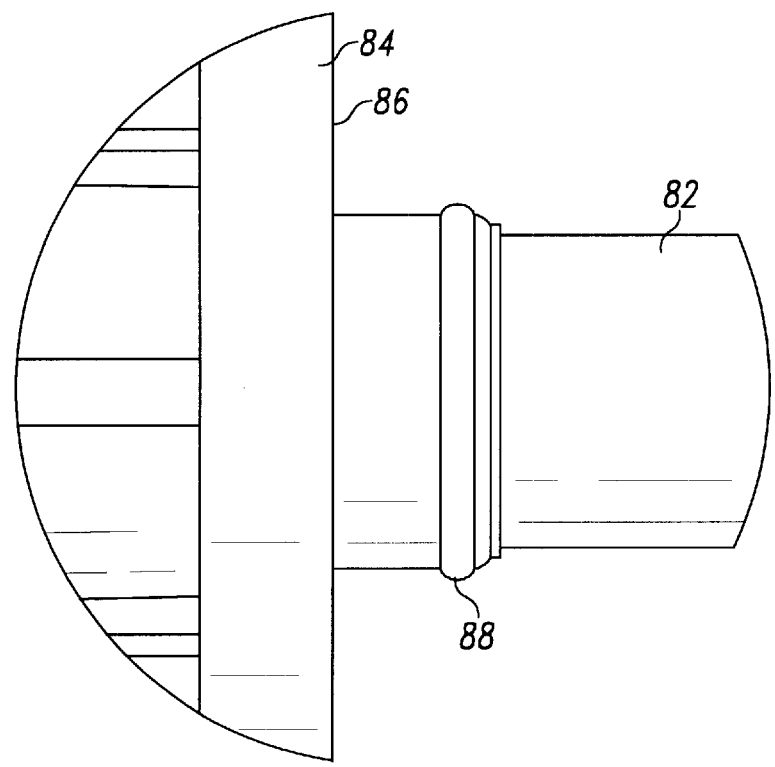
FIG. 10 is an enlarged elevation detail of the dilator hub shown in FIG. 9 showing the engaging ring feature.

FIGS. 9 and 10 show a side elevation view of a dilator hub 80 suitable for use with the T-shaped fitting 10 of the present invention. The dilator hub 80 includes a tubular portion 82 intended to be received within the sheath 22. A radially extending flange 84 includes a distal surface 86 designed to contact the top surface 25 of the T-shaped fitting 10. A peripheral extension 88 situated forward of distal surface 86 is intended to be received in that portion of the opening 20 defined by surface 54. As the dilator hub 80 is pressed into engagement with the T-shaped fitting 10, the ring 88 will snap past the projections 52 and provide a tactile and/or auditory signal of coupling engagement between the hub 80 and the fitting 10. Thereafter, suitable instrumentation may be coupled to the proximal end 90 and inserted through tubular portion 82 of the hub 80. Once the instrumentation is suitably in place, a physician may choose to remove the sheath 22 by simply breaking the handles 12 and 14 of the T-shaped fitting 10 apart from each other. As the handles 12 and 14 are separated from each other, the tabs 34 and 36 of the bifurcated proximal end of the sheath 22 cause a tension on the initial split of the sheath 22 thereby causing the sheath to tear apart in a known manner.

While the foregoing description illustrates a preferred embodiment of the present invention, it will be apparent to those skilled in the art that other variations modifications are contemplated which come within the scope of the following claims.

What is claimed is:

1. A splittable sheath assembly comprising:
   a sheath adapted for use in the trans-cutaneous insertion of medical instrumentation through a lumen defined by the sheath, the sheath having a distal end and a proximal end, the proximal end including an initial bifurcated portion defining two tabs,
   a T-shaped fitting having a central opening aligned with the lumen of the sheath, a handle on either side of the central opening, and a zone of weakness separating the two handles so that the T-shaped fitting is adapted to be split into two separate portions, each portion having only one of the handles, and
   attachment mechanisms formed separately from the T-shaped fitting, each attachment mechanism including a projection engaging a portion of one of the tabs and a locking element received over the projection to inhibit movement of the tab relative to the projection, the attachment mechanisms being encapsulated in the handles of the T-shaped fitting to attach each of the tabs of the proximal end of the sheath to one of the handles.

2. The assembly of claim 1 wherein each locking element of the attachment mechanisms includes an innermost end spaced outwardly from the central opening.

3. The assembly of claim 1 wherein the projection of each attachment mechanism includes a piercing end portion for penetrating the tab contiguous thereto.

4. The assembly of claim 1 wherein the projection of each attachment comprises a series of teeth received in interdental spaces on the corresponding locking element.

5. The assembly of claim 1 wherein the projection of each attachment comprises ridges received in furrows situated on the corresponding locking element.

6. The assembly of claim 1 further comprising raised areas on an inside surface of the central opening of the T-shaped fitting for engagement with said medical instrumentation.

7. The assembly of claim 6 further comprising a dilator hub having a peripheral engagement ring situated on a forward portion of the hub snap fit into engagement with said raised areas in the central opening of the T-shaped fitting.

8. The assembly of any of claims 1–7 further comprising a hinge portion coupling the projection and the locking element of the attachment mechanism together.

9. The assembly of claim 8 wherein the hinge portion, projection and locking element comprise a unitary structure.

10. The assembly of claim 9 wherein the attachment mechanism further comprises an axially directed portion positioned contiguous to the central opening in the T-shaped fitting, and a laterally outwardly extending portion containing the projection, hinge portion and locking element.

11. The assembly of claim 8 wherein the hinge portion is positioned at an outer lateral extremity of the attachment mechanism.

12. The assembly of any of claims 1–7 wherein the projection extends proximally in a direction substantially parallel to the central opening in the T-shaped fitting.

13. A splittable sheath assembly comprising:
   a sheath adapted for use in the trans-cutaneous insertion of medical instrumentation through a lumen defined by the sheath, the sheath having a distal end and a proximal end, the proximal end including an initial bifurcated portion defining two tabs,
   a T-shaped fitting having a central opening aligned with the lumen of the sheath, a handle on either side of the central opening, and a zone of weakness separating the two handles so that the T-shaped fitting is adapted to be split into two separate portions, each portion having only one of the handles, raised areas on an inside surface of the central opening generally aligned with the zone of weakness of the T-shaped fitting for engagement with said medical instrumentation, and attachment mechanisms for attaching each of the tabs of the proximal end of the sheath to one of the handles, each attachment mechanism including a projection engaging a portion of one of the tabs and a locking element received over the projection to inhibit movement of the tab relative to the projection, the attachment mechanisms being encapsulated in the handles of the T-shaped fitting.

14. The assembly of any of claims 1–7 further comprising a plurality of ridges on a proximal surface of each handle.

15. The assembly of any of claims 1–7 wherein the zone of weakness comprises longitudinal v-shaped slots on each side of the T-shaped fitting orthogonal to the handles.

16. The assembly of any of claims 1–7 wherein outer extremities of the handles are larger than portions closer to the central opening so that the handles of the T-shaped assembly have a butterfly conformation.

17. The assembly of any of claims 1–7 wherein the sheath includes scoring aligned with the zone of weakness.

18. The assembly of any of claims 1–7 where the sheath comprises TFE tubing having a longitudinal molecular orientation.

19. A method of making a splittable sheath and splittable handle assembly comprising the steps of:

molding attachment mechanisms having a first portion including a projection and a second portion to be received over the projection;

providing a sheath having a distal end and a proximal end, the proximal end including an initial bifurcated portion defining two tabs;

fixing each of the tabs between the first and second portions of an attachment mechanism, and subsequent to the fixing step, embedding the attachment mechanisms into a T-shaped handle having an opposed pair of zones of weakness that facilitate the T-shaped handle being split into two separate parts, the embedding of the attachment mechanisms being such that each part of the T-shaped handle contains only one of the attachment mechanisms.

20. The method of claim 19 wherein the embedding step comprises the steps of inserting the attachment mechanisms into a mold and injection molding the T-shaped handle around the attachment mechanisms.

21. The method of claim 19 wherein the embedding step further comprising the steps of forming the T-shaped handle to include a central opening aligned with the proximal end of the sheath, the central opening having raised areas on an inside surface for engagement with other medical instrumentation.

22. A method of making a splittable sheath and splittable handle assembly comprising the steps of:

molding attachment mechanisms having a first portion including a projection and a second portion to be received over the projection;

providing a sheath having a distal end and a proximal end, the proximal end including an initial bifurcated portion defining two tabs;

fixing each of the tabs between the first and second portions of an attachment mechanism, embedding the attachment mechanisms into a T-shaped handle having an opposed pair of zones of weakness that facilitate the T-shaped handle being split into two separate parts, the embedding of the attachment mechanisms being such that each part of the T-shaped handle contains only one of the attachment mechanisms, the embedding step further comprising the steps of forming the T-shaped handle to include a central opening aligned with the proximal end of the sheath, the central opening having raised areas on an inside surface for engagement with other medical instrumentation, the raised areas within the central opening being formed to be generally aligned with the zones of weakness of the T-shaped fitting.

23. The method of any of claims 19–22 wherein the fixing step comprises impaling each tab with one of the projections of the first portion and covering the impaled tab with the second portion.

24. The method of claim 23 wherein the covering step includes locking the second portion of the attachment mechanism to first portion.

25. The method of any of claims 19–22 wherein the molding step comprises forming an intervening unitary hinge portion between first and second portions of each attachment mechanism.

26. The method of claim 25 wherein the fixing step further includes folding the second portion of the attachment mechanism over the first portion.

27. The method of any of claims 19–22 wherein the providing step comprises the step of extruding TFE tubing under conditions whereby the tubing acquires a longitudinal molecular orientation facilitating a splitting action.

28. The method of claim 19 wherein the embedding step comprises the steps of inserting the attachment mechanisms with the tabs fixed thereto into a mold and compression molding the T-shaped handle around the attachment mechanisms.

29. The method of claim 19 wherein the embedding step further comprises the steps of forming the T-shaped handle to include a central opening aligned with the proximal end of the sheath, and spacing the attachment mechanism from the central opening.

* * * * *